(12) United States Patent
Jörg et al.

(10) Patent No.: US 8,305,086 B2
(45) Date of Patent: Nov. 6, 2012

(54) FLAME IONIZATION DETECTOR

(75) Inventors: Müller Jörg, Hamburg (DE); Winfred Kuipers, Hamburg (DE)

(73) Assignee: Bayer Technology Services GmbH, Leverkusen (DE)

( * ) Notice: Subject to any disclaimer, the term of this patent is extended or adjusted under 35 U.S.C. 154(b) by 381 days.

(21) Appl. No.: 12/675,470

(22) PCT Filed: Aug. 18, 2008

(86) PCT No.: PCT/EP2008/006781
§ 371 (c)(1),
(2), (4) Date: Feb. 26, 2010

(87) PCT Pub. No.: WO2009/036854
PCT Pub. Date: Mar. 26, 2009

(65) Prior Publication Data
US 2010/0301870 A1 Dec. 2, 2010

(30) Foreign Application Priority Data
Sep. 13, 2007 (EP) .................................... 07018014

(51) Int. Cl.
*G01N 27/62* (2006.01)
(52) U.S. Cl. .......... 324/464; 422/54; 340/577; 340/579; 436/154
(58) Field of Classification Search .................... 324/464
See application file for complete search history.

(56) References Cited

U.S. PATENT DOCUMENTS

| 5,576,626 | A | * | 11/1996 | Lo | .................................. | 324/464 |
| 6,193,501 | B1 | * | 2/2001 | Masel et al. | .................. | 431/170 |
| 6,701,774 | B2 | * | 3/2004 | Srinivasan et al. | ........... | 73/23.42 |

(Continued)

FOREIGN PATENT DOCUMENTS
WO 2006/000099 A1 1/2006

OTHER PUBLICATIONS

Zimmermann S. et al. "Micro Flame inoization Detector and micro Flame Spectrometer" Sensors and Actutors B, Elsevier Sequoia S.A., Lausanne, CH vol. 63, No. 3, May 2000, pp. 159-166, XP004198335 ISSN: 0925-4005.

(Continued)

*Primary Examiner* — Timothy J Dole
*Assistant Examiner* — Benjamin M Baldridge
(74) *Attorney, Agent, or Firm* — Norris McLaughlin & Marcus, P.A.

(57) ABSTRACT

The flame ionization detector, which comprises a supply and an ignition device (7) for the combustible gas, a supply for the sample gas, a combustion chamber (4) in which the sample gas is ionized by the flame, and electrodes (8, 1) to which a voltage is applied in order to generate and measure the ion current, is distinguished in that it is constructed as an integrated planar system of at least three parallel platelet-like substrates (1, 2, 3) which are connected to one another and are processed by microsystem technology methods, with a central substrate (1) comprising nozzles (5, 6) for the gases and the ignition device (7) and a recess which forms a part of the combustion chamber (4), is completed by recesses in the neighboring substrates (2, 3) and is essentially closed together with the nozzle region by these substrates (2, 3), and the neighboring substrates (2, 3) comprise supply channels (10, 11) for the gases.

12 Claims, 3 Drawing Sheets

U.S. PATENT DOCUMENTS

| | | | |
|---|---|---|---|
| 6,786,716 B1* | 9/2004 | Gardner et al. | 431/268 |
| 7,046,012 B2* | 5/2006 | Dean et al. | 324/459 |
| 7,077,643 B2* | 7/2006 | Holladay et al. | 431/215 |
| 7,273,517 B1* | 9/2007 | Lewis et al. | 96/101 |
| 2003/0006778 A1* | 1/2003 | Aiki et al. | 324/464 |
| 2005/0093551 A1* | 5/2005 | Weyl et al. | 324/464 |
| 2007/0057179 A1* | 3/2007 | Bousse et al. | 250/288 |

OTHER PUBLICATIONS

R. Manginell et al., "Micro Flame-Based Detector Suite for Universal Gas Sensing" Sandia report, No. SAND2005-6236, 2005, Sandia National Laboratories, Albuquerque, New Mexico, US The whole document.

Stefan Zimmermann et al., "Miniaturized flame ionization detector for gas chromatography" Sensors and actuators B 83 (2002) 285-289 The whole document, Jan. 29, 2002.

Zimmermann S. et al. "Micro Flame inoization Detector and micro Flame Spectrometer" Sensors and Actutors B, Elsevier Sequoia S.A., Lausanne, CH vol. 63, No. 3, May 2000, pp. 159-166, XP004198335 ISSN: 0925-4005 (document not provided).

R. Manginell et al., "Micro Flame-Based Detector Suite for Universal Gas Sensing" Sandia report, No. SAND2005-6236, 2005, Sandia National Laboratories, Albuquerque, New Nexico, US The whole document (document not provided).

* cited by examiner

FLAME IONIZATION DETECTOR

This is an application filed under 35 USC §371 of PCT/EP2008/006781, claiming priority to EP 07018014.6 filed Sep. 13, 2007.

BACKGROUND OF THE INVENTION

The invention relates to a flame ionization detector (FID) which comprises a supply and an ignition device for the combustible gas, a supply for the sample gas, a combustion chamber in which the sample gas is ionized by the flame, and electrodes to which a voltage is applied in order to generate and measure the ion current.

Flame ionization detectors are used to detect and measure volatile organic compounds in gaseous samples. The measurement is based on the chemical ionization of organic substances, which are pyrolyzed in an oxyhydrogen gas flame. An ionization reaction of the carbon atoms contained in the substance takes place:

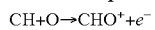

$$CH + O \rightarrow CHO^+ + e^-$$

When a voltage is applied to an electrode pair arranged at the edge of the flame, an ion current flows which can be measured and used to detect the organic compounds. If the gas is first passed through a gas chromatograph, for example a capillary gas chromatograph, then the various chemical compounds of the sample gas enter the flame ionization detector in succession, sorted according to molecular weight, so that the concentration of the different components can be established.

A problem with flame ionization detectors is that it is necessary to supply oxyhydrogen gas, a highly explosive mixture of oxygen and hydrogen. It is therefore desirable to make the flame ionization detectors as small as possible so that only small quantities of oxyhydrogen gas are required, and the explosion risk is therefore reduced. Furthermore, such small flame ionization detectors are naturally advantageous since they are easier to transport and take up less space. In addition, the lower consumption of oxyhydrogen gas allows it to be produced in situ by electrolysis instead of being used in a stored form, which further reduces the explosion risk. One such flame ionization detector, which makes use of this advantage, consists of components that are produced according to the methods of microsystem technology (S. Zimmermann et al., "Microflame ionization detector and microflame spectrometer", Sensors and Actuators B63 (2000), pp. 159-166; S. Zimmermann et al., "Miniaturized flame ionization detector for gas chromatography", Sensors and Actuators B83 (2000), pp. 285-289). The oxyhydrogen flame in this case burns in open space, and is enclosed only by a metallized glass tube which forms an electrode pair together with the silicon substrate. Since the flame burns in open space, the result can be influenced by turbulence and contamination. Heat is furthermore radiated, so that a comparatively large quantity of combustible gas is required. An additional disadvantage is that the glass tube must be adhesively bonded, and therefore the detector cannot be produced entirely by the methods of microsystem technology, so that its structure is elaborate and expensive and unsuitable for mass production.

Other previously known flame ionization detectors with a small design have the disadvantage that they cannot be produced, or cannot be produced entirely, by the methods of microsystem technology (U.S. Pat. No. 5,576,626; WO 2006/000099 A1).

BRIEF SUMMARY OF THE INVENTION

It is an object of the invention to provide a flame ionization detector which has a small size and can be produced entirely by the methods of microsystem technology.

According to the invention, the flame ionization detector is characterized in that it is constructed as an integrated planar system of at least three parallel platelet-like substrates which are connected to one another and are processed by microsystem technology methods, with a central substrate comprising nozzles for the gases and the ignition device and a recess which forms a part of the combustion chamber, is completed by recesses in the neighboring substrates and is essentially closed together with the nozzle region by these substrates, and the neighboring substrates comprise supply channels for the gases.

The flame ionization detector according to the invention thus consists essentially of three platelet-like substrates, although further substrates could be provided. These substrates are produced exclusively using microsystem technology means, by photoetching and the like. The central substrate comprises nozzles for the gases and the ignition device, and a recess which forms a part of the combustion chamber. The combustion chamber is completed by recesses in the neighboring substrates. While the central substrate may be open all the way through in the region of the combustion chamber, the neighboring substrates comprise walls which close the combustion chamber after assembly. The combustion chamber is therefore essentially closed. "Essentially closed" means that the combustion chamber merely has to comprise a small opening through which the gases can escape outward. It would even be conceivable to close the combustion chamber entirely, if a cooling device is provided on which the only combustion product, i.e. water, can condense. It would then merely be necessary to provide suitable measures by which the water can be removed.

The two neighboring or outer substrates, however, enclose not only the combustion chamber but also the nozzle region. While the nozzles for the combustible gas and the sample gas are provided in the central substrate, these gases are supplied through supply channels into the neighboring outer substrates.

In an advantageous embodiment, the central substrate is electrically conductive and the neighboring substrates are essentially nonconductive. "Essentially nonconductive" means that the conductivity is low even at elevated temperature, but still high enough for anodic bonding of the substrates to be possible, which does in fact presuppose a certain conductivity of the components. This conductivity should not however be too high since leakage currents, which can vitiate the measurement result, would then occur in addition to the ion currents which are intended to be measured.

Advantageously, the central substrate consists of silicon and the neighboring substrates consist of glass, borosilicate glass in particular having proven to be particularly advantageous as the glass.

In an advantageous embodiment, an electrode is arranged in each of the neighboring substrates in the region of the combustion chamber. There are therefore electrodes on both sides of the combustion chamber. The disadvantage with this is that not only the ion current is measured when a voltage is applied to the two electrodes, but also the current which flows from one electrode to the other owing to the non-zero conductivity of the outer substrates, and water which has condensed.

This disadvantage can be avoided by a shielding electrode according to the invention, by which these currents are collected. In an advantageous embodiment, on the one hand one electrode is formed by the central substrate and on the other hand the shielding electrode in addition to the second electrode is located on one of the two neighboring substrates, between the two electrodes. Currents which flow from one neighboring substrate to the other neighboring substrate will in this case be collected by the shielding electrode and not also measured.

Owing to the high temperature of the flame (up to 2700° C.), the flame ionization detector is heated strongly. In order to avoid stress cracks, all the parts expediently have rounded contours.

If the electrodes on the neighboring substrates are rendered reflective, the heat from the flame will be reflected back into the combustion chamber. On the one hand, less combustible gas will be required. On the other hand, the detector will be heated less.

In an advantageous embodiment, the nozzles for the gases are formed as a buried structure and are covered by at least one further substrate. In this way, it is possible to achieve a symmetrical arrangement of the nozzles.

Advantageously, the central substrate comprises at least one electrode tip immediately behind the nozzles. Via this electrode tip and an electrode on one of the two neighboring substrates, a high-voltage pulse can be applied in order to ignite the flame. Such high-voltage pulses could, for example, be generated by a piezo crystal. The flame ionization detector may also be used to generate electrical energy, by providing it with two high-induction magnets and thereby forming a magnetohydrodynamic generator.

The invention will be explained below with the aid of advantageous embodiments with reference to the appended drawings, in which:

DETAILED DESCRIPTION OF THE INVENTION

Figure 1:
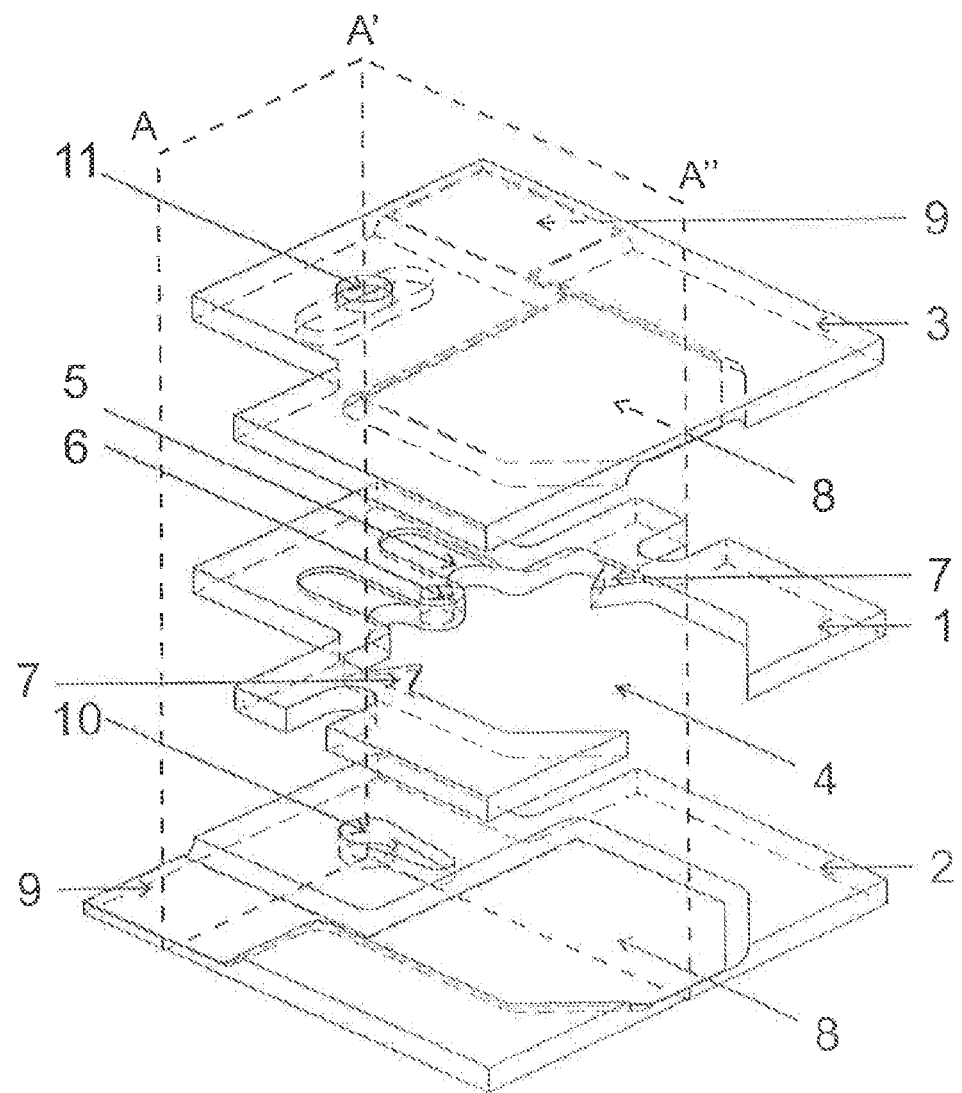
FIG. 1 shows an exploded view of an embodiment of the flame ionization detector according to the invention.

FIG. 1 shows an exploded view of an inventive embodiment of the flame ionization detector. It comprises three substrates: a central substrate 1 made of silicon, and a lower substrate 2 and an upper substrate 3 which are made of Pyrex glass. A part of the combustion chamber 4, the sample gas nozzle 5 and the combustible gas nozzle 6 are excavated in the central substrate 1 by known microsystem technology methods. Acute projections 7, which extend into the combustion chamber 4 in the vicinity of the nozzles 5, 6, can have a high-voltage pulse applied to them for ignition.

The lower substrate 2 and the upper substrate 3 are provided with trough-shaped recesses in the region of the combustion chamber 4, and these are provided with a reflective metallization 8. The metallization 8 is connected to bonding lands 9, through which the electrical connection can take place. The substrate 2 lying underneath in the figures also comprises a combustible gas inlet 10, while the upper substrate 3 comprises a sample gas inlet 11. After the three substrates have been connected by anodic bonding, these inlets are in communication with the nozzles 5, 6.

Figure 2:
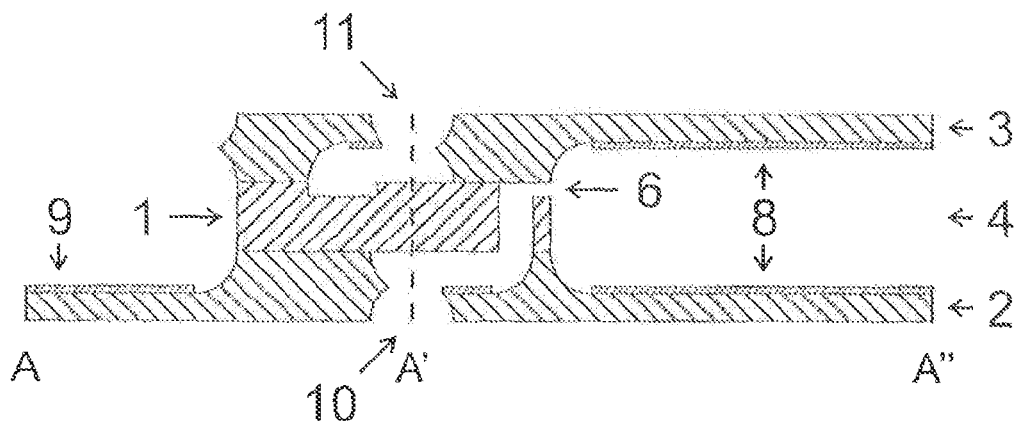
FIG. 2 shows a sectional view along the angled line A-A'-A" in FIG. 1.
Figure 3:
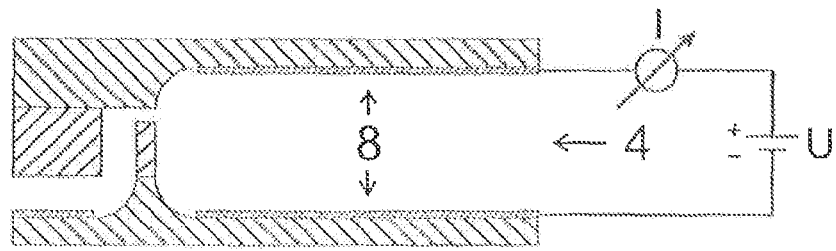
FIG. 3 shows a measuring arrangement in section, in a representation corresponding to FIG. 2.

FIG. 2 shows a sectional view along the angled line A-A'-A" in FIG. 1. The combustible gas and the sample gas enter the combustion chamber 4, which is provided with the metallizations 8, through corresponding channels. These metallizations may be used as the electrodes, on which a voltage is applied and the current is measured, as schematically represented in FIG. 3. A disadvantage with this is that the voltage source U generates not only an ion current between the two electrodes 8, which is measured at I, but also on the one hand a current due to the limited conductivity of the substrates 1, 2 and 3 as well as a current which is brought about by the condensed moisture.

Figure 4:
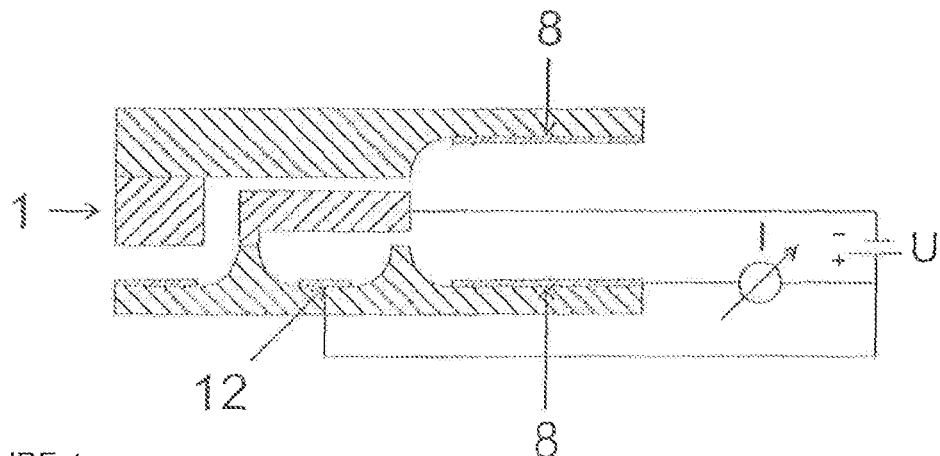
FIG. 4 shows a second particularly advantageous embodiment of the measuring arrangement in section, in a representation corresponding to FIG. 2.
Figure 5:
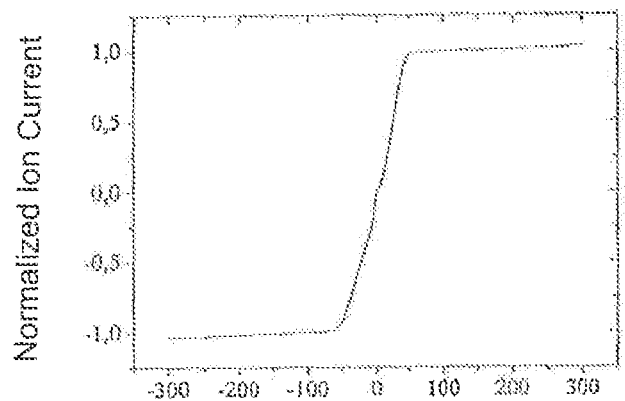
FIG. 5 shows the dependency of the ion current on the applied voltage in an advantageous embodiment.

This advantage is avoided in the embodiment according to FIG. 4 by a shielding electrode 12. Only one of the metallizations 8, i.e. the one underneath in FIG. 12, is electrically connected. The other metallization merely has the purpose of reflecting heat back into the combustion chamber 4, so that less combustible gas is required. The substrate 1 is used as the second electrode for the measurement. The shielding electrode 12 is connected via the voltage source U to the substrate 1. Currents which flow outside the combustion chamber (before the gases reach the combustion chamber), specifically because of the conductivity of the substrates and condensed water and owing to the voltage source U, will not however also be measured by the ammeter I. Instead, only the currents between the substrate 1 and the lower electrode 8 will be measured, that is to say only the currents which are actually caused by the flame ionization.

The flame ionization detector according to the invention can be made very small. Typically, it occupies a footprint of 10×10 mm. The substrates only need to have a thickness of less than 100 µm. The nozzle openings for the combustible gas and the gas to be measured can be reduced to a few tens to 100 µm², so as to minimize the combustible gas consumption or optimize the gas mixing. Although the combustion chamber 4 is shown as open toward the right in the figures, it will normally be closed except for a small opening in order to avoid turbulence due to external air flows and contamination. Diffusion back from the surroundings may for example be prevented by the combustion chamber 4 communicating with the surroundings only through a narrow gap, for instance between the central substrate and one or both neighboring cover substrates, or through a narrow gap in the central substrate. The combustion chamber could be closed entirely with water in which the combustion product, i.e. water, condenses on an additional cooling device.

As mentioned, the flame ionization detector may be produced by using the conventional techniques of microsystem technology and photolithography.

Figure 6:
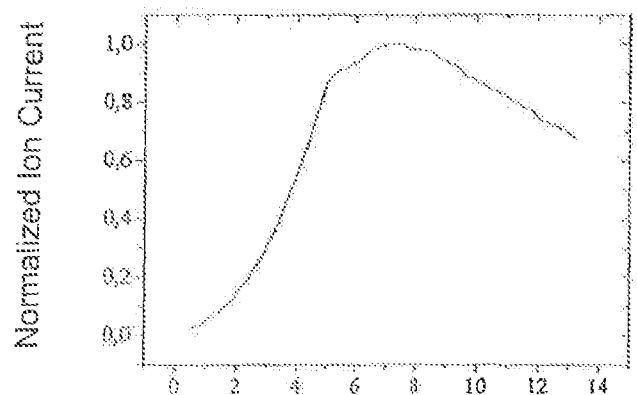
FIG. 6 shows the dependency of the ion current on the flow rate of the sample gas.

A typical flame ionization detector according to the invention operates with comparatively low voltages, as shown in FIG. 6. Saturation already takes place with a voltage of plus or minus 50 V. The measurement result is then constant at higher voltage values. The corresponding curve was recorded with a sample gas flow of 7 ml/min. The dependency of the ion current on the flow rate of the sample gas with a voltage of 100 V is shown in FIG. 7.

The invention claimed is:
1. A flame ionization detector comprising:
a supply and an ignition device (7) for a combustible gas,
a supply for a sample gas,
a combustion chamber (4) wherein the sample gas is ionized by a flame, electrodes (8, 1) situated inside the combustion chamber, to which a voltage is applied for generating and measuring an ion current,
wherein the detector is constructed as an integrated planar system of at least three parallel planar substrates (1, 2, 3)

that are bonded to one another in a sandwich configuration, wherein a central substrate (1) comprises nozzles (5, 6) for the gases and the ignition device (7) and a recess which forms a part of the combustion chamber (4), and wherein the combustion chamber is formed by recesses in a top and bottom substrate (2, 3) and is essentially closed together with the nozzle region by the top substrate and the bottom substrate (2, 3), the top and bottom substrates (2, 3) comprise supply channels (10, 11) for the gases.

2. The flame ionization detector as claimed in claim 1, wherein the central substrate (1) is electrically conductive and the neighboring substrates (2, 3) are essentially nonconductive.

3. The flame ionization detector as claimed in claim 1, wherein central substrate (1) consists of silicon and the neighboring substrates (2, 3) consist of glass, in particular borosilicate glass.

4. The flame ionization detector as claimed in claim 1, wherein an electrode (8) is arranged in each of the neighboring substrates (2, 3) in the region of the combustion chamber (4).

5. The flame ionization detector as claimed in claim 2, wherein one electrode is formed by the central substrate (1).

6. The flame ionization detector as claimed in claim 5, wherein the central substrate comprises a shielding electrode (12).

7. The flame Ionization detector as claimed in claim 1, wherein all the substrates (1, 2, 3) comprise parts with rounded contours.

8. The flame ionization detector as claimed in claim 1, wherein the substrates (1, 2, 3) are connected by anodic bonding.

9. The flame ionization detector as claimed in claim 4, wherein the electrodes (8) on the neighboring substrates (1, 2) are reflective.

10. The flame Ionization detector as claimed in claim 1, wherein the nozzles (5, 6) for the gases are formed as a buried structure and are covered by at least one further substrate.

11. The flame Ionization detector as claimed in claim 1, wherein the central substrate (1) comprises at least one electrode tip (7) immediately behind the nozzles (5, 6), to which a high-voltage pulse is being applied for ignition.

12. The flame ionization detector as claimed in claim 1, wherein the detector is provided with two high-induction magnets for forming a magneto-hydrodynamic generator.

\* \* \* \* \*